US005813401A

United States Patent [19]

Radcliff et al.

[11] Patent Number: 5,813,401

[45] Date of Patent: Sep. 29, 1998

[54] NEBULIZER AUTOMATIC CONTROL VALVE

[76] Inventors: Janet H. Radcliff, 160 Foxshire Dr., Lancaster, Pa. 17601; Gordon R. Hostetter, 1634 Campus Rd., Eliabethtown, Pa. 17022; Meyric K. Rogers, 1037 Woods Ave., Lancaster, Pa. 17603; Gregg M. Bair, 40 Holly Dr., Leola, Pa. 17540

[21] Appl. No.: 732,774

[22] Filed: Oct. 15, 1996

[51] Int. Cl.[6] .................... A61H 16/00

[52] U.S. Cl. .................... 128/205.24; 128/207.12; 128/200.14; 128/200.24; 128/203.12

[58] Field of Search .................... 128/205.24, 207.12, 128/207.16, 200.14, 200.18, 200.21, 200.23, 200.24, 203.12

[56] References Cited

U.S. PATENT DOCUMENTS

| | | | |
|---|---|---|---|
| 1,109,318 | 9/1914 | Browne et al. | 128/205.24 |
| 2,432,946 | 12/1947 | Theunissen | 128/200.14 |
| 3,769,973 | 11/1973 | Esbenshade, Jr, | 128/200.14 |
| 4,174,712 | 11/1979 | Moren et al. | 128/200.14 |
| 4,259,951 | 4/1981 | Chernack et al. | 128/200.14 |
| 4,823,784 | 4/1989 | Bordoni et al. | 128/200.14 |
| 5,020,530 | 6/1991 | Miller | 128/200.21 |
| 5,062,419 | 11/1991 | Rider | 128/200.14 |
| 5,165,392 | 11/1992 | Small, Jr. | 128/200.21 |
| 5,396,883 | 3/1995 | Knupp et al. | 128/200.14 |
| 5,398,673 | 3/1995 | Lambert | 128/205.22 |
| 5,427,089 | 6/1995 | Kraemer | 128/200.14 |

*Primary Examiner*—John G. Weiss
*Assistant Examiner*—V. Srivastava
*Attorney, Agent, or Firm*—Martin Fruitman

[57] ABSTRACT

The invention is a control valve for a nebulizer for inhalation therapy which stops the supply of mist except when the patient is actually inhaling. The preferred structure is a "T" shaped configuration with the lower end mounted atop the nebulizer and one end of the horizontal breath tube used as a mouthpiece. A shuttle cylinder with a check valve slides axially within the breath tube and includes a hole which aligns with the feed tube when the shuttle is at the end toward the patient. In that position the shuttle permits the mist to reach the patient through the shuttle. However, when the patient exhales, the shuttle moves to the opposite end of its travel and closes off the supply of mist while permitting the exhaled air to exit.

25 Claims, 7 Drawing Sheets

PRIOR ART

NEBULIZER AUTOMATIC CONTROL VALVE

BACKGROUND OF THE INVENTION

This invention deals generally with a medical apparatus, and more specifically with the control of a nebulizer, a device for supplying medicated and atomized liquid for inhalation.

A number of pulmonary medications prescribed for patients with chronic or acute lung disease are delivered in aerosol form. This method of delivery of medications is fast, efficient, and effective, with less systemic side effects than other forms of delivery of medication. The medications are atomized and delivered by inhalation directly to the lung tissue. Patients who benefit from this therapy include those with asthma, bronchitis, emphysema, and acute infections such as pneumonia. Aerosol medications can be given to patients in a variety of locations, including hospitals, physician's offices, pulmonary function laboratories, or at home by self administration. This means of medication delivery is also increasingly applicable to non-pulmonary medicines using the respiratory mucosa as a means for systemic deep delivery.

Typically such medications are delivered to the patient by means of a small volume nebulizer powered by an air compressor or oxygen source at flow rates of 6–8 liters per minute. However, the problem with most such nebulizers is that the medication is delivered to the mouthpiece of the apparatus continuously during the entire treatment, even though the medication is only actually used and delivered to the lung tissue when the patient inhales. At other times during the respiratory cycle, when the patient is not actually inhaling, including when the patient is coughing or talking, the medication is still typically being expelled into the surrounding environment. Therefore, a considerable amount of medication is wasted by being lost to the surrounding environment, and also other nearby people, including medical personnel, can be unintentionally exposed to the effects of the medication.

One device which has been used to counteract this problem is a nebulizer which includes a finger port to control the air pressure for atomization of the medication. In such a device there is a simple hole in the duct delivering oxygen or compressed air to the atomizer. When such a hole is covered by the patient's finger, the air supply is fed to the atomizer and the system acts normally. However, when the hole is uncovered the air supply vents to the atmosphere, and no medication is supplied to the patient.

Although such a device seems at first to be a solution to the waste of medication, it still has problems. Perhaps the most important problem is that such a device requires coordination which is beyond the capability of many patients, but it should also be apparent that the device also uses the pressurized air source continuously, and when the source is limited, as when it uses a portable oxygen tank, this is also a problem.

SUMMARY OF THE INVENTION

The present invention solves the problem of nebulizers which deliver medication continuously by using the patient's breathing cycle to automatically control the delivery of medication to the lungs. The invention is a very simple control valve for a nebulizer for drug delivery. This control valve is attached to a typical nebulizer, where the aerosol supply has already been produced, and the valve blocks the flow of mist to the patient except when the patient is actually inhaling.

The structure of the preferred embodiment is two intersecting tubes, one feed tube and one breath tube. One end of the feed tube is mounted on and connected to the output of a nebulizer which is driven by a source of compressed air or a source of oxygen. The other end of the feed tube opens into the interior of the breath tube. One end of the breath tube of the valve structure is open and used as a mouthpiece while a hole in the breath tube acts as a breath outlet and is located approximately opposite the junction with the feed tube.

An internal shuttle cylinder with an open interior and including a check valve is located within the breath tube. This shuttle cylinder slides axially within the breath tube and can include an arrangement to mate with the breath tube in order to prevent rotation or removal of the shuttle from the breath tube. The shuttle also includes a hole which aligns with the feed tube from the nebulizer when the shuttle is as far toward the patient as it is allowed to move.

In the position nearest to the patient the shuttle permits the mist to reach the inhaling patient because the atomized medication flows from the nebulizer, up the feed tube, into the shuttle through the hole in the shuttle, through the optional front check valve, and to the patient's mouth at the open end of the breath tube. The shuttle is drawn to the position nearest to the patient by the patient's action of inhaling, because the shuttle acts as a pneumatic piston reacting to the patient's inhalation until the shuttle hits an end stop as flow from the nebulizer and through the shuttle begins.

However, when the patient exhales, the pressure from the exhalation closes the check valve and moves the shuttle, again acting as a pneumatic piston, to the opposite end of its travel. This stops the supply of mist because the hole into the shuttle is no longer aligned with the open end of the feed tube. As the shuttle moves to the end of the breath tube remote from the patient, the end of the shuttle also clears the output hole in the breath tube to permit the exhaled air to exit from the valve assembly. When the patient then inhales again the shuttle moves back toward the patient, and the cycle continues to repeat as the patient breathes.

The shuttle movement and the check valve opening are powered only by the patient inhaling and exhaling. The only requirement for proper operation of the control valve of the invention is that the force required to move the shuttle and the force required to open the check valve be attainable by the patient breathing. These conditions can easily be met by reducing the friction of the shuttle's movement by such means as thin ribs protruding from the shuttle's outer surface, so that the contact surface between the shuttle and the breath tube walls is minimized. Similarly, controlling the force required to open the check valve only requires selecting the proper resisting force for the check valve.

The present invention thereby furnishes a nebulizer control valve which permits the flow of medication only when the patient is actually inhaling the medicated aerosol, and therefore it prevents the waste of medication and minimizes the exposure of others to the medication.

DETAILED DESCRIPTION OF THE INVENTION

Figure 1:
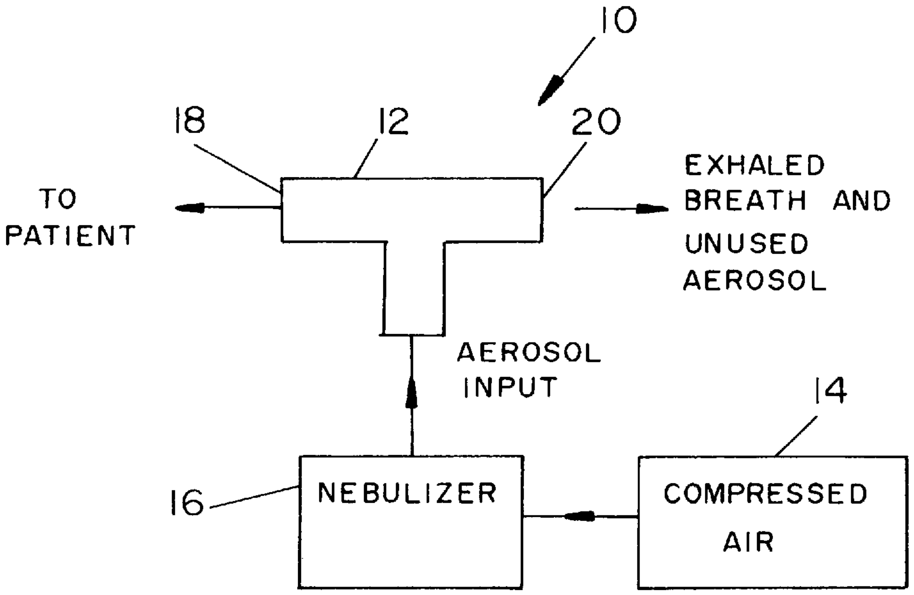
FIG. 1 is a schematic diagram a typical prior art apparatus in which the invention is substituted.

FIG. 1 is a schematic diagram of a typical prior art nebulizer apparatus 10 in which the present invention can be substituted for mouthpiece 12. Such a nebulizer apparatus is driven by compressed air source 14 which could also be a source of oxygen. Compressed air from source 14 is supplied to nebulizer 16 which contains a supply of liquid medication, and the air atomizes the medication and produces an aerosol which the air pressure pushes into mouthpiece 12. The patient, whose mouth is applied to end 18 of mouthpiece 12, then inhales the aerosol produced within the nebulizer. Mouthpiece 12 of the prior art is usually a simple hollow tube "T" configuration.

As previously discussed, the nebulizers of the prior art generally operate continuously so that even when the patient is not inhaling the aerosol is still being produced and is being expelled from mouthpiece 12 along with the exhaled air at end 20 of mouthpiece 12.

Figure 2:
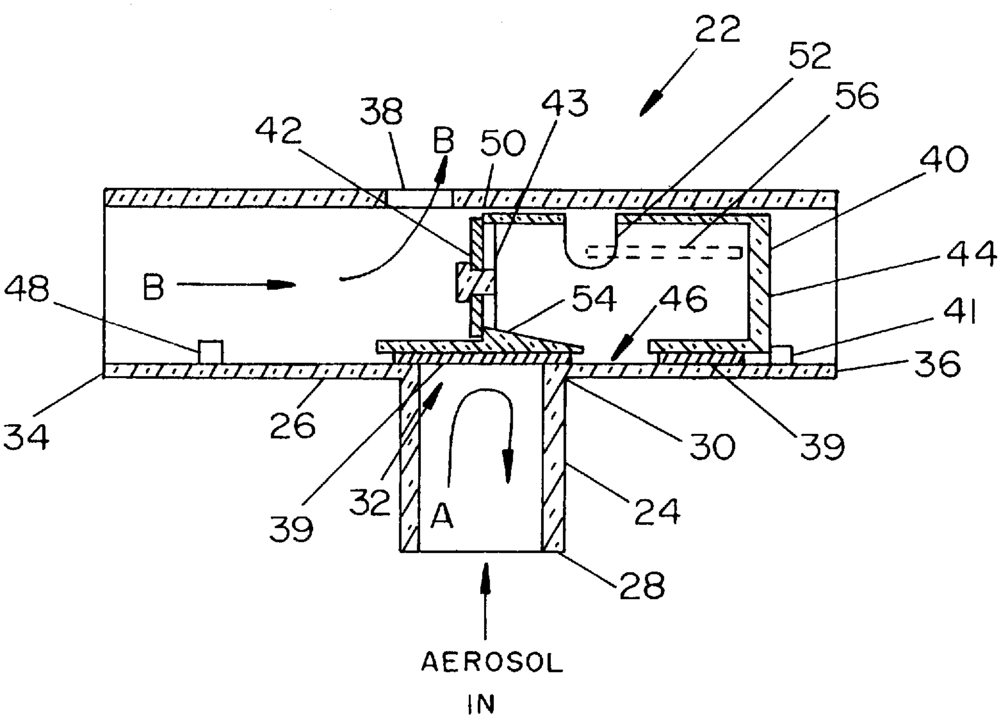
FIG. 2 is a cross section side view of the preferred embodiment of the invention along the axis of the breath tube shown in the condition when the patient exhales.
Figure 3:
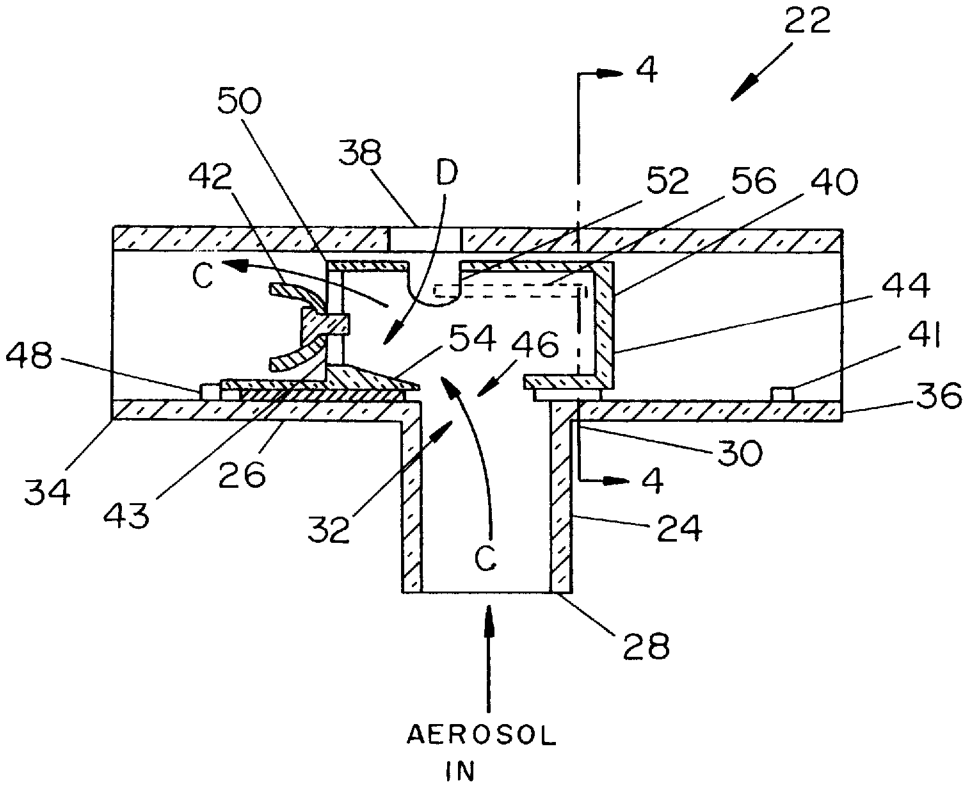
FIG. 3 is a cross section side view of the preferred embodiment of the invention along the axis of the breath tube shown in the condition when the patient inhales.

Nebulizer control valve 22 shown in FIG. 2 and FIG. 3 operates to eliminate the waste of medication by preventing the aerosol from being expelled into the environment when the patient is not inhaling the aerosol. FIG. 2 and FIG. 3 depict the same structure of the preferred embodiment of nebulizer control valve 22 in a cross section side view in two different conditions. Control valve 22 is typically formed from plastic and is essentially two tubes, one feed tube 24 and one breath tube 26, oriented in the shape of a "T". The lower end 28 of feed tube 24 is mounted on and connected to the output of a nebulizer (not shown) which is driven by a source of compressed air or a source of oxygen (not shown) in the same manner as mouthpiece 12 of FIG. 1.

Upper end 30 of feed tube 24 opens into the interior of breath tube 26 at opening 32. One end 34 of breath tube 26 is open and used as a mouthpiece, and the opposite end 36 of breath tube 26 is also open enough to provide access to atmospheric pressure. Outlet hole 38 in the breath tube acts as a breath outlet and is located approximately opposite the junction of breath tube 26 with feed tube 24.

Hollow internal shuttle cylinder 40 is located within breath tube 26 and includes check valve 42 at one end, end wall 44 at the other end, and hole 46 approximately midway between its ends. Check valve 42 is held in position by open web 43 so that flow is not obstructed. Shuttle cylinder 40 slides axially within breath tube 26 on thin ribs 39 (also seen if FIG. 4), which in the preferred embodiment are only 0.010 inch high. This minimal height minimizes the air leakage around shuttle cylinder 40, but also minimizes the contact friction between shuttle cylinder 40 and the inner walls of breath tube 26.

In the position shown in FIG. 2, as the patient is exhaling, check valve 42 is closed, shuttle cylinder 40 is as far from the patient as end stop 41 permits, and shuttle cylinder 40 closes off opening 32 at end 30 of feed tube 24 preventing aerosol from leaving feed tube 24, as shown by arrow A in FIG. 2. Also, when shuttle cylinder 40 is in the position shown in FIG. 2 shuttle 40 permits direct access from end 34 to hole 38 within breath tube 26, thus permitting unimpeded exhalation of the patient's breath as shown by arrows B in FIG. 2.

When the patient inhales, check valve 42 opens as shown in FIG. 3, and the difference in pressure across end wall 44 of shuttle 40, which is caused by atmospheric pressure on the outside and the slight vacuum created by the the patient's inhalation on the inside, causes shuttle 40 to move to the position shown in FIG. 3. This position is determined by stop 48 located within breath tube 26. As shuttle 40 approaches stop 48, hole 46 aligns with opening 32 of feed tube 24.

In this position shown in FIG. 3 shuttle 40 permits the aerosol to reach the inhaling patient because, as shown by arrow C, the atomized medication flows from the nebulizer, through feed tube 24, into shuttle 40 through open end 32 and hole 46, through check valve 42, and to the patient's mouth at open end 34 of breath tube 26.

Then, when the patient exhales, the pressure from the exhalation closes check valve 42 and moves shuttle 40 to the opposite end of its travel against stop 41 as shown in FIG. 2. This once more stops the supply of aerosol because hole 46 into shuttle 40 is no longer aligned with open end 32 of feed tube 24. As shuttle 40 moves toward end 36 of breath tube 26, end 50 of the shuttle also clears output hole 38 in breath tube 26 to permit the exhaled air to exit from valve 22. When the patient then inhales again the shuttle moves back toward the patient, and the cycle continues to repeat as the patient breathes.

FIG. 2 and FIG. 3 show an additional optional feature of the invention in supplementary air hole 52. With air hole 52 in shuttle 40 located as shown in FIG. 3 to align with hole 38, the inhaling patient is supplied with supplementary air. As shown by arrow D, this air moves through shuttle 40 and check valve 42 to the patient while mixing with the medicated aerosol.

Another optional feature of the invention is drain ramp 54 within the interior of shuttle 40. As can be seen in FIG. 3, this lower surface which slopes from check valve 42 toward hole 46 allows liquid which may accumulate within shuttle 40 to drain back into feed tube 24, from which it will return to the nebulizer and again be atomized.

Figure 4:
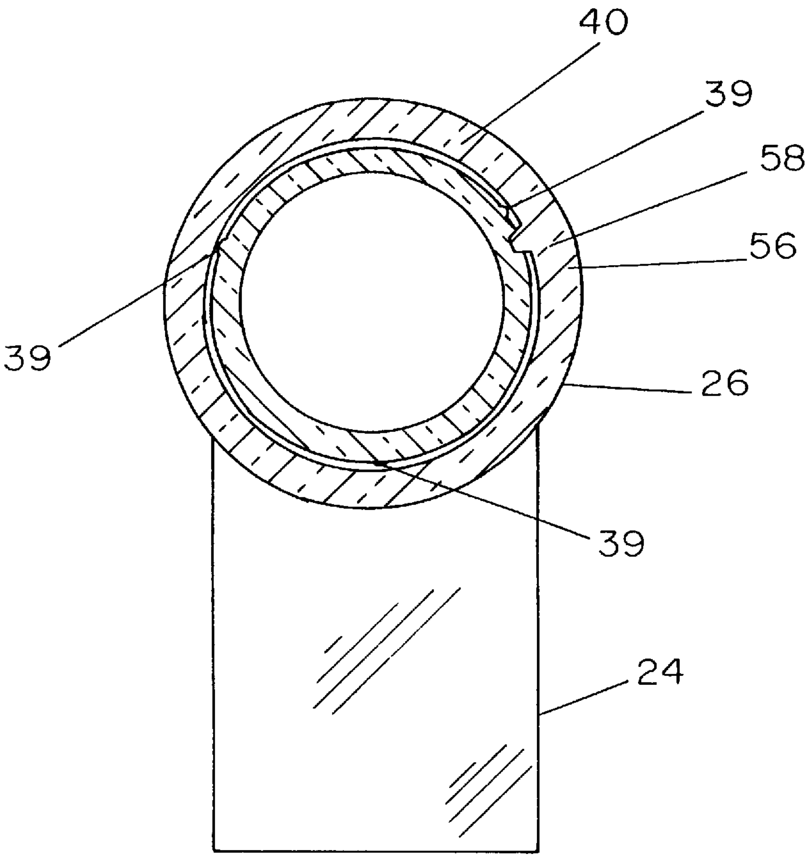
FIG. 4 is a cross section view of the preferred embodiment of the invention at the section lines 4—4 of FIG. 3.

FIG. 4 is a cross section view of the preferred embodiment of the invention at section lines 4—4 of FIG. 3, and shows that shuttle cylinder 40 fits inside breath tube 26 to form an air seal and prevent significant leakage between the surfaces. FIG. 4 also shows slot 56 on the outside surface of shuttle cylinder 40 into which is fitted tab 58 which extends from the inside surface of breath tube 26. This slot and tab arrangement, which, of course, could also have the tab extending from shuttle cylinder 40, prevents shuttle cylinder 40 from rotating and causing misalignment of the various holes. Another advantage of the slot and tab arrangement is that it can substitute for end stops 41 and 48. When slot 56 has closed ends as shown in FIG. 2 and FIG. 3 and tab 58 is properly positioned, the movement of shuttle cylinder 40 will be stopped when the end of the slot hits the tab.

Figure 5:
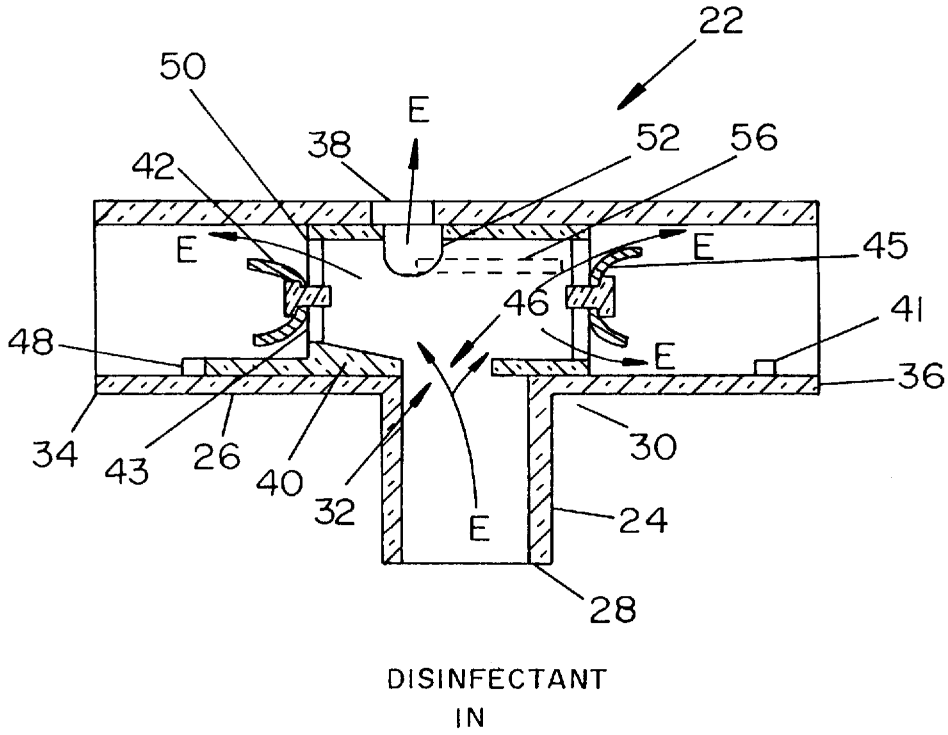
FIG. 5 is a cross section side view of an alternate embodiment of the invention along the axis of the breath tube showing a second check valve at the end of the shuttle remote from the patient.

FIG. 5 is a cross section side view of an alternate embodiment of the invention along the axis of breath tube 26 showing second check valve 45 at the end of the shuttle remote from the patient. Check valve 45 is similar in construction and function to check valve 42, but is located at the opposite end of shuttle cylinder 40 from check valve 42. The function of check valve 45 is to facilitate disinfection of nebulizer control valve 22. The position of check valve 45 assures that when disinfectant is pumped into feed tube 24 it will pass through all portions of nebulizer control valve 22, as indicated by arrows E in FIG. 5. Without check valve 45, both bacteria and disinfectant might be trapped by the closed end 44 of shuttle cylinder 40 (FIG. 3). Check valve 45 is constructed so that it remains closed during normal operation of nebulizer control valve 22 because the pressure from the nebulizer is insufficient to open it, and during the inhalation by the patient the pressure differential is oriented to keep it closed. However, when disinfectant is applied under higher pressure, check valve 45 opens to furnish complete access to and flow through shuttle cylinder 40.

Figure 6:
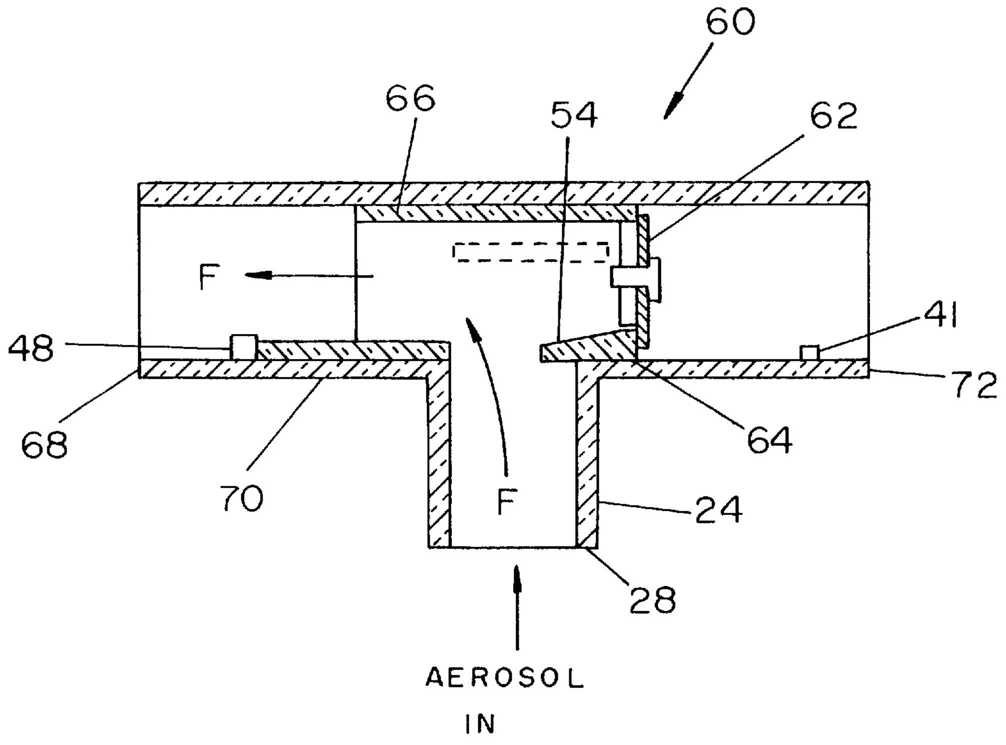
FIG. 6 is a cross section side view of an alternate embodiment of the invention along the axis of the breath tube using only one check valve at the end of the shuttle remote from the patient.

FIG. 6 is a cross section view of an alternate embodiment of the invention in which nebulizer control valve 60 uses only a single check valve 62 located at remote end 64 of shuttle 66. FIG. 6 shows what is perhaps the simplest of the embodiments of the invention as it appears in the position for inhalation of aerosol by the patient. Control valve 60 operates similarly to the previous embodiments described in that, in the position shown, aerosol is delivered to mouthpiece end 68 of breath tube 70, as shown by arrows F. When the patient exhales, the pressure against check valve 62 first moves shuttle cylinder 66 to remote end 72 of breath tube 70, against stop 41, and then opens check valve 62 fully to expel the exhaled breath.

Nebulizer control valve 60 requires reduced shuttle friction, and it is also desirable to use a check valve with a two stage operation to encourage movement of shuttle 66 first and subsequent full opening of check valve 62. It should be noted that FIG. 6 does not use ribs on the outside surface of shuttle 66 to reduce friction. This is possible by the use of low friction materials for the construction of both breath tube 70 and shuttle 66.

Figure 7:
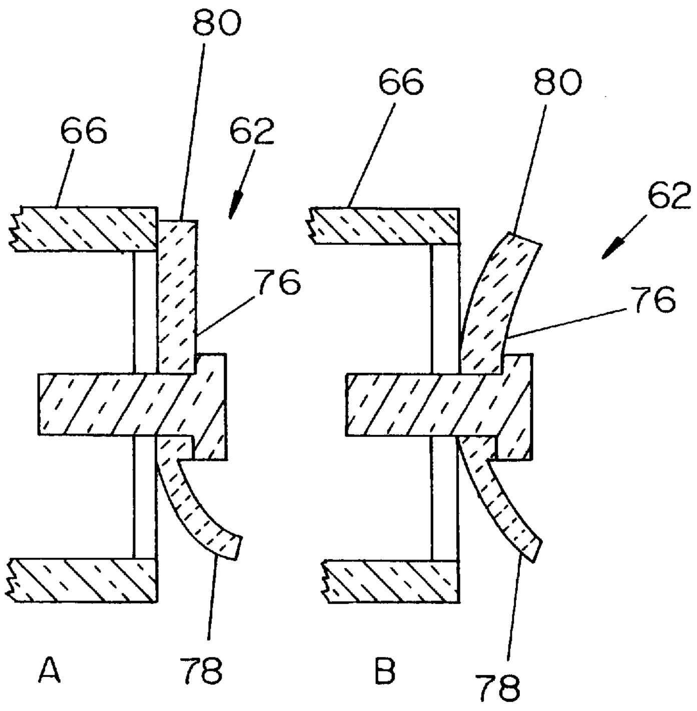
FIG. 7 is a cross section view of an embodiment of check valve 62 of FIG. 6.

FIG. 7 is a cross section view of an embodiment of check valve 62 of FIG. 6 which affords two stage operation desirable for using single check valve 62 at the remote end of the shuttle. Check valve 62 has diaphragm 76 with two sections of different stiffness. Section 78 is a thin section and that permits it to open first, as shown in FIG. 7A, at a lower pressure. Such a partial opening permits shuttle 66 to move with exhalation by the patient because thicker section 80 of diaphragm 76 remains closed and affords a greater surface area against which the exhalation pressure operates. Nevertheless, when shuttle 66 is stopped at the end of the breath tube, section 80 then opens as shown in FIG. 7B to permit full expulsion of the exhalation.

As can be appreciated from the description above, the nebulizer control valve of the invention is controlled and powered only by the breathing of the patient, yet it assures that medication will be efficiently used, and that none will be expelled into the environment.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

For example, the specific locations of check valve 42, hole 46, hole 52 and groove 56 can be varied. Furthermore, the invention can be interconnected with a nebulizer by flexible tubing rather than feed tube 24 being attached directly to the nebulizer. It is also possible to use check valves other than the specific type pictured, for instance, a simple hinged flap could be used for the check valve, and it could be placed in a different location in the shuttle. Moreover, the invention can be constructed in a configuration other than the "T" structure pictured, particularly when flexible tubing is used for the connection to the nebulizer.

What is claimed as new and for which Letters Patent of the United States are desired to be secured is:

1. A control valve for a nebulizer comprising:

a straight hollow tube having an open patient's end, an opening to surrounding atmosphere located remote from the patient's end, a feed hole in the tube wall through which medicated aerosol can be supplied, and an exhalation hole in the tube wall; and a straight hollow shuttle, with the shuttle positioned within the tube so that the shuttle is adjacent to the tube wall and slides back and forth within the tube in a region between the patient's end and the opening, the shuttle including:

a closed end remote from the patient's end of the tube, an inlet hole in the shuttle wall, with the shuttle constructed and the inlet hole located so that when the shuttle is in a first position, the inlet hole and the feed hole are aligned, and the exhalation hole is closed off by the shuttle, and when the shuttle is in a second position which is more remote from the patient's end of the tube than the first position, the tube closes off the inlet hole, the shuttle closes off the feed hole, and the exhalation hole is open, and a check valve located within the shuttle in a position between the inlet hole and the patient's end and operating to permit flow only from within the shuttle out to the patient's end of the tube;

wherein the shuttle is located close enough to the tube wall and the sliding friction between the shuttle and the tube wall is maintained low enough so that the pressure of a user's exhalation and the vacuum of a user's inhalation is sufficient to move the shuttle back and forth within the tube.

2. The control valve of claim 1 wherein the tube and the shuttle are both cylinders.

3. The control valve of claim 1 further including end stop means attached to the tube to determine the location of the first and second positions of the shuttle.

4. The control valve of claim 1 wherein the tube and the shuttle are sliding parts and further including a slot in a wall of one of the sliding parts and a mating tab attached to a wall of the other sliding part to prevent relative rotation of the parts.

5. The control valve of claim 4 wherein the slot has closed ends and the tab functions as the stop means.

6. The control valve of claim 1 wherein the check valve is located at the end of the shuttle nearest to the patient's end of the tube.

7. The control valve of claim 1 wherein the opening is an open end of the tube remote from the patient's end.

8. The control valve of claim 1 further including an air hole in a wall of the shuttle which aligns with the exhalation hole when the shuttle is in the first position to furnish additional air to the patient.

9. The control valve of claim 1 wherein the inlet hole is located in the bottom of the shuttle and further including an inclined surface located between the check valve and the inlet hole, with the portion of the inclined surface nearer to the check valve higher than the portion near the inlet hole.

10. The control valve of claim 1 wherein a rigid feed tube is attached to the tube at the feed hole.

11. The control valve of claim 10 wherein the tube and the feed tube form a "T" structure.

12. The control valve of claim 1 wherein the closed end of the shuttle is closed by a second check valve which opens to the atmosphere when the pressure within the shuttle is greater than the pressure within the shuttle during breathing by a patient.

13. The control valve of claim 1 further including ribs between the shuttle and the tube so that the sliding friction between the shuttle and the tube is reduced.

14. A control valve for a nebulizer comprising:

a straight hollow tube having an open patient's end, an opening to surrounding atmosphere located remote from the patient's end, and a feed hole in the tube wall through which medicated aerosol can be supplied; and a straight hollow shuttle, with the shuttle positioned within the tube so that the shuttle is adjacent to the tube wall and slides back and forth in a region between the patient's end and the opening, the shuttle including an inlet hole in the shuttle wall, with the shuttle constructed and the inlet hole located so that when the shuttle is in a first position, the inlet hole and the feed hole are aligned, and when the shuttle is in a second position which is more remote from the patient's end of the tube than the first position, the tube closes off the inlet hole, and the shuttle closes off the feed hole, and a check valve located within the shuttle in a position on the opposite side of the inlet hole from the patient's end and operating to permit flow only from within the shuttle out to the opening;

wherein the shuttle is located close enough to the tube wall and the sliding friction between the shuttle and the tube wall is maintained low enough so that the pressure of a user's exhalation and the vacuum of a user's inhalation is sufficient to move the shuttle back and forth within the tube.

15. The control valve of claim 14 wherein the tube and the shuttle are both cylinders.

16. The control valve of claim 14 further including end stop means attached to the tube to determine the location of the first and second positions of the shuttle.

17. The control valve of claim 14 wherein the tube and the shuttle are sliding parts and further including a slot in a wall of one of the sliding parts and a mating tab attached to a wall of the other sliding part to prevent relative rotation of the parts.

18. The control valve of claim 17 wherein the slot has closed ends and the tab functions as the stop means.

19. The control valve of claim 14 wherein the check valve is located at the end of the shuttle remote from the patient's end of the tube.

20. The control valve of claim 14 wherein the opening is an open end of the tube remote from the patient's end.

21. The control valve of claim 14 wherein the inlet hole is located in the bottom of the shuttle and further including an inclined surface located between the check valve and the inlet hole, with the portion of the inclined surface nearer to the check valve higher than the portion near the inlet hole.

22. The control valve of claim 14 wherein a rigid feed tube is attached to the tube at the feed hole.

23. The control valve of claim 22 wherein the tube and the feed tube form a "T" structure.

24. The control valve of claim 14 further including ribs between the shuttle and the tube so that the sliding friction between the shuttle and the tube is reduced.

25. The control valve of claim 14 wherein the check valve is constructed so that it opens in two stages, with one part of the check valve opening at a lower pressure than a second part.

* * * * *